United States Patent
Patrick et al.

(10) Patent No.: US 9,821,008 B2
(45) Date of Patent: Nov. 21, 2017

(54) INHIBITORS OF ERCC1-XPF AND METHODS OF USING THE SAME

(71) Applicant: The University of Toledo, Toledo, OH (US)

(72) Inventors: Stephan M. Patrick, Toledo, OH (US); Paul W. Erhardt, Toledo, OH (US); Christopher Trabbic, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 15/038,585

(22) PCT Filed: Nov. 25, 2014

(86) PCT No.: PCT/US2014/067289
§ 371 (c)(1),
(2) Date: May 23, 2016

(87) PCT Pub. No.: WO2015/077753
PCT Pub. Date: May 28, 2015

(65) Prior Publication Data
US 2016/0296556 A1    Oct. 13, 2016

Related U.S. Application Data

(60) Provisional application No. 61/908,431, filed on Nov. 25, 2013.

(51) Int. Cl.
*A61K 33/24* (2006.01)
*A61K 31/185* (2006.01)
(Continued)

(52) U.S. Cl.
CPC ............ *A61K 33/24* (2013.01); *A61K 31/185* (2013.01); *A61K 31/255* (2013.01); *A61K 45/06* (2013.01); *C07C 309/47* (2013.01); *C07C 309/67* (2013.01); *C07C 309/73* (2013.01); *C07C 317/36* (2013.01); *C07C 323/66* (2013.01)

(58) Field of Classification Search
CPC .............................. A61K 33/24; A61K 31/185
See application file for complete search history.

(56) References Cited

U.S. PATENT DOCUMENTS 5,633,016 A  *  5/1997  Johnson  ............... A61K 31/282
                                                            424/649

FOREIGN PATENT DOCUMENTS

EP       2599480 A1      6/2013
GB       819 320     *   9/1959
(Continued)

OTHER PUBLICATIONS

Vogelstein and Kinzler, The Genetic Basis of Human Cancer, 2nd ed., 2002, p. 3.*
(Continued)

*Primary Examiner* — San-Ming Hui
(74) *Attorney, Agent, or Firm* — MacMillan, Sobanski & Todd, LLC

(57) ABSTRACT

Compositions and methods for inhibiting the DNA repair protein complex, ERCC1-XPF, and methods to enhance clinical responses to anticancer drugs that interact with DNA such as cisplatin, and to overcome drug resistance due to DNA repair mechanisms, are described.

12 Claims, 3 Drawing Sheets

(51) Int. Cl.
- *A61K 45/06* (2006.01)
- *A61K 31/255* (2006.01)
- *C07C 309/47* (2006.01)
- *C07C 309/67* (2006.01)
- *C07C 309/73* (2006.01)
- *C07C 317/36* (2006.01)
- *C07C 323/66* (2006.01)

(56) References Cited

FOREIGN PATENT DOCUMENTS

| GB | 819320 | 9/1959 |
|---|---|---|
| WO | 2006/127978 A2 | 11/2006 |
| WO | 2012/135831 A1 | 10/2012 |

OTHER PUBLICATIONS

Calabresi and Chabner, Goodman & Gilman's The Pharmacological Basis of Therapeutics, 10th ed., 2001, p. 1388.*

Arora et al., "Identification of small molecule inhibitors of ERCC1-XPF that inhibit DNA repair and potentiate cisplatin efficacy in cancer cells", Oncotarget, Advance Publications, 2016, pp. 1-14.

Barakat et al., "Characterization of an inhibitory dynamic pharmacophore for the ERCC1-XPA interaction using a combined molecular dynamics and virtual screening approach", Journal of Molecular Graphics and Modelling, 2009, vol. 28, pp. 113-130.

Calabresi et al., "Chemotherapy of Neoplastic Diseases", Goodman & Gilmans's The Pharmacological Basis of Therapeutics, Tenth Edition, 2001, pp. 1381-1388.

"2-Naphthalenecarboxylic acid, 4-methyl-", Chemical Abstract RN 5773-87-5, Web accessed May 12, 2017.

"2-Naphthalenecarboxylic acid, 4-ethyl-", Chemical Abstract RN 13188-34-6, Web accessed May 12, 2017.

Cobo et al., "Customizing Cisplatin Based on Quantitative Excision Repair Cross-Complementing 1 mRNA Expression: A Phase III Trail in Non-Small-Cell Lung Cancer", Journal of Clinical Oncology, 2007, vol. 25, No. 19, pp. 2747-2754.

Cuyas et al., "Oncometabolic mutation IDH1 R132H confers a metformin-hypersensitive phenotype", Oncotarget, 2015, vol. 6, No. 14, pp. 12279-12296.

Jordheim et al., "Small Molecule Inhibitors of ERCC1-XPF Protein-Protein Interaction Synergize Alkylating Agents in Cancer Cells", Molecular Pharmacology, 2013, vol. 84, pp. 12-24.

McNeil et al., "DNA repair endonuclease ERCC1-XPF as a novel therapeutic target to overcome chemoresistance in cancer therapy", Nucleic Acids Research, 2012, vol. 40, No. 20, pp. 9990-10004.

"Kyselina o-tosyl-h", PubChem Compound, NSC16168, Web accessed Jan. 22, 2015, pp. 1-3.

Vogelstein, "Chapter 1—Introduction", The Genetic Bases of Human Cancer, 2nd Edition, 2002, pp. 1-3.

Extended European Search Report, Application No. EP 14863805.9, dated May 24, 2017.

PCT International Search Report and the Written Opinion, Application No. PCT/US2014/067289 filed Nov. 25, 2014, dated Mar. 17, 2015.

* cited by examiner

| Cell Line | Combination Factor |
|---|---|
| 2008/C13*5.25 ovarian cancer | ~4 µM |
| H460 lung cancer | ~7-8 µM |

INHIBITORS OF ERCC1-XPF AND METHODS OF USING THE SAME

This application claims the benefit of PCT/2014/067289 filed Nov. 25, 2014, which claims priority to U.S. Provisional Application No. 61/908,431, filed under 35 U.S.C. §111(b) on Nov. 25, 2013, the entire disclosure of which is expressly incorporated herein by reference

STATEMENT REGARDING FEDERALLY SPONSORED RESEARCH

This invention was not made with any government support. The government has no rights in the invention.

TECHNICAL FIELD AND INDUSTRIAL APPLICABILITY OF THE INVENTION

Described herein are compositions and methods for the treatment of anti-proliferative diseases, including cancer, which involve administering to a mammalian species in need thereof: (1) at least one inhibitor of a DNA repair enzyme, and (2) a therapeutic agent that kills cancer cells via interaction with cellular DNA.

BACKGROUND OF THE INVENTION

It is estimated that approximately 22,000 new cases of ovarian cancer will be diagnosed in 2012 (American Cancer Society Statistics). These patients typically undergo a combination of surgery, chemotherapy and radiation treatment. Many of the current chemotherapeutic drugs bind to, or are incorporated into, DNA, which ultimately blocks DNA replication and transcription. The accumulation of damaged DNA blocks cell progression that leads to an apoptotic response.

One of the limitations of chemotherapy in ovarian cancer, however, is that many cancers have innate drug resistance or acquire drug resistance. There are several mechanisms responsible for the development of drug resistance, including decreased drug accumulation, increased drug inactivation/sequestering by thiols, and increased DNA repair. Increased DNA repair has been shown to be a major mechanism of cancer drug resistance, including in patient samples following cisplatin treatment. The enhanced DNA repair that is observed in cancers occurs early in the development of resistance, appears to be one of the first mechanisms activated, and it is evident in nearly all cases of high cisplatin resistance.

With respect to chemotherapy and effects on cancer treatment, repair of the damaged DNA induced by the chemotherapy is detrimental to the efficacy of the drugs. This is supported by the fact that DNA repair deficient cells are hypersensitive to many chemotherapeutic agents, including cisplatin.

Ovarian cancer is typically treated with a combination of surgery and chemotherapy. One of the biggest problems in regard to killing the ovarian cancer cells is drug resistance. This resistance can be seen prior to the initial treatment or as a consequence of drug therapy. Many chemotherapeutic drugs, including cisplatin, function by binding to DNA and inhibiting cells from replicating and dividing. This ultimately inhibits cancer cell growth and leads to cell death. Ovarian cancers, as well as other cancers that are resistant to cisplatin, often have pathways in place or develop ways to remove the drug from DNA to avoid cell death. DNA repair pathways can be up-regulated in resistant cancers and remove cisplatin from the DNA.

With respect to cisplatin DNA repair, nucleotide excision repair (NER) is the primary pathway for the removal of the abundant intrastrand DNA adducts. It is now believed that both NER and homologous recombination (HR) play critical roles in the repair of cisplatin DNA interstrand crosslinks (ICLs).

Cells typically have multiple mechanisms and pathways to deal with the chemotherapeutic drugs directed toward killing tumors. The current chemotherapeutic drugs do not selectively target cancer cells which, as a consequence, typically leads to toxic side effects by targeting normal cells. If a particular cancer is mutated in one of two pathways required for the repair of a specific chemotherapeutic agent, then by targeting the other pathway, the cancers would be selectively targeted with chemotherapy.

In this scenario, normal cells will be minimally affected and have reduced side effects as the alternate pathway of drug removal is still functional. One way to selectively target cancer cells is to take advantage of specific mutations that have arisen as a consequence of tumorigenesis and loss of heterozygosity (LOH).

In spite of considerable research into therapies to treat such diseases, it remains difficult to treat effectively, and the mortality observed in patients indicates that improvements are needed in the diagnosis, treatment and prevention of such diseases.

SUMMARY OF THE INVENTION

Described herein is a method of treating a subject suffering from a cell proliferative disorder, comprising administering to a cell in need thereof an effective amount of at least one anti-proliferative agent that kills the cell via interacting with DNA, and at least one inhibitor of a DNA repair enzyme. In certain embodiments, the cell over-expresses the DNA repair enzyme ERCC1-XPF. In certain embodiments, the anti-proliferative agent comprises a DNA cross-linking compound. In certain embodiments, the DNA cross-linking compound comprises a platinum-containing anti-neoplastic compound. In certain embodiments, the platinum-containing anti-neoplastic compound comprises one or more of: cisplatin, carboplatin, oxaliplatin, satraplatin, picoplatin, nedaplatin and triplatin.

Described herein is a method of treating a subject suffering from a cell proliferative disorder, comprising administering to a cell in need thereof at least one anti-proliferative agent that kills cells by interacting with DNA, and at least one compound of Formula I, or a stereoisomer, optical isomer, a pharmaceutically acceptable salt, or a pharmaceutically acceptable solvate thereof:

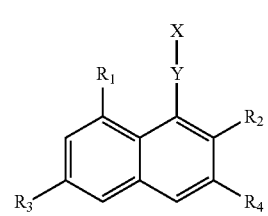

Formula I wherein: X=alkyl, alkenyl, alkynyl, aryl, or heteroaryl; wherein alkyl is from 1 to 5 carbons, alkenyl is from 2 to 6 carbons, alkynyl is from 2 to 6 carbons, aryl is from 6 to 12 carbons and includes aralkyl, heteroaryl is from 5 to 12 atoms and includes heteroalkyl, and wherein for all cases each system may be further substituted with hydroxy or amino groups;

Y=$(CH_2)_n$ where n=0 to 3, CHCH, $CH_2$CHCH, CHCHCH$_2$, CC, $CH_2$CC, $CCCH_2$, O, NH, S, (SO), O(CO), (CO)O, O(CO)O, NH(CO), (CO)NH, NH(CO)NH, O(CO)NH, NH(CO)O, O($SO_2$), ($SO_2$)O, O($SO_2$)O, NH($SO_2$), ($SO_2$)NH, NH($SO_2$)NH, O(HOPO), (HOPO)O, O(HOPO)O, O(HOPO)NH, NH(HOPO)O, or NH(HOPO)NH;

$R_1$ and $R_2$ together or independently=H, alkyl, alkenyl, alkynyl, halogen, OH, $OR_5$, where $R_5$=alkyl, $NH_2$, $NHR_5$, $NR_5R_5$, or $NO_2$;

$R_3$ and $R_4$ together or independently=H providing both are not H, $CO_2H$, $CO_2X$, $SO_3H$, $SO_3X$, (HOPO)OH, or (HOPO)OX.

In certain embodiments, X is an aralkyl group consisting of para-methylphenyl, Y is ($SO_2$)O, $R_1$ is $NH_2$, $R_2$ is H, and $R_3$=$R_4$ are both $SO_3H$.

Described herein is a compound having Formula I:

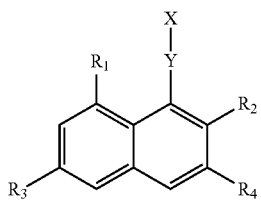

Formula I wherein: X=alkyl, alkenyl, alkynyl, aryl, or heteroaryl; wherein alkyl is from 1 to 5 carbons, alkenyl is from 2 to 6 carbons, alkynyl is from 2 to 6 carbons, aryl is from 6 to 12 carbons and includes aralkyl, heteroaryl is from 5 to 12 atoms and includes heteroalkyl, and wherein for all cases each system may be further substituted with hydroxy or amino groups;

Y=$(CH_2)_n$ where n=0 to 3, CHCH, $CH_2$CHCH, CHCHCH$_2$, CC, $CH_2$CC, $CCCH_2$, O, NH, S, (SO), O(CO), (CO)O, O(CO)O, NH(CO), (CO)NH, NH(CO)NH, O(CO)NH, NH(CO)O, O($SO_2$), ($SO_2$)O, O($SO_2$)O, NH($SO_2$), ($SO_2$)NH, NH($SO_2$)NH, O(HOPO), (HOPO)O, O(HOPO)O, O(HOPO)NH, NH(HOPO)O, or NH(HOPO)NH;

$R_1$ and $R_2$ together or independently=H, alkyl, alkenyl, alkynyl, halogen, OH, ORS, where $R_5$=alkyl, $NH_2$, $NHR_5$, $NR_5R_5$, or $NO_2$;

$R_3$ and $R_4$ together or independently=H providing both are not H, $CO_2H$, $CO_2X$, $SO_3H$, $SO_3X$, (HOPO)OH, or (HOPO)OX.

In certain compounds, X is an aralkyl group consisting of para-methylphenyl, Y is ($SO_2$)O, $R_1$ is $NH_2$, $R_2$ is H, and $R_3$=$R_4$ are both $SO_3H$.

Described herein is a method for treating a subject having a cell proliferation disorder with an inadequate response to an anti-proliferative agent, comprising administering to the subject an effective amount of at least one compound of Formula I, or a stereoisomer, optical isomer, a pharmaceutically acceptable salt, or a pharmaceutically acceptable solvate thereof, thereby treating the subject.

Described herein is a method of enhancing the therapy of a subject who has become resistant to therapeutic effects of anti-proliferative agents that kill cancer cells via interacting with DNA, comprising administering to the subject an effective amount of at least one compound of Formula I, or a stereoisomer, optical isomer, a pharmaceutically acceptable salt, or a pharmaceutically acceptable solvate thereof, thereby treating the subject.

Described herein is a method for treating cell proliferation disorder in a subject in need of such treatment, comprising administering to the subject an effective amount of at least one compound of Formula I, or a stereoisomer, optical isomer, a pharmaceutically acceptable salt, or a pharmaceutically acceptable solvate thereof, thereby treating the subject. In certain embodiments, the cell proliferation disorder comprises a cancer. In certain embodiments, the cancer is ovarian cancer. In certain embodiments, the subject is human. In certain embodiments, the method further comprises administering at least one anti-proliferative agent. In certain embodiments, the anti-proliferative agent comprises a platinum containing compound.

Described herein is a method for the treatment of proliferative diseases, including cancer, which comprises administering to a mammalian specie in need thereof at least one anti-proliferative agent, and at least one DNA repair enzyme inhibitor compound of Formula I, or a stereoisomer, optical isomer, a pharmaceutically acceptable salt, or a pharmaceutically acceptable solvate thereof. In certain embodiments, the anti-proliferative agent is administered following administration of the DNA repair enzyme inhibitor compound. In certain embodiments, the anti-proliferative agent is administered prior to the administration of the DNA repair enzyme inhibitor compound. In certain embodiments, the anti-proliferative agent is administered simultaneously with the DNA repair enzyme inhibitor compound. In certain embodiments, the method is for the treatment of cancerous solid tumors. In certain embodiments, the method is for the treatment of refractory tumors.

Described herein is a pharmaceutical composition for the treatment of cancer which comprises at least one anti-proliferative agent and at least one DNA repair enzyme inhibitor compound of Formula I, or a stereoisomer, optical isomer, a pharmaceutically acceptable salt, or a pharmaceutically acceptable solvate thereof, and a pharmaceutically acceptable carrier. In certain embodiments, the composition is useful for the treatment of cancerous solid tumors. In certain embodiments, the composition is useful for the treatment of refractory tumors.

Described herein is a method of modulating drug resistance in a cancer subject in need thereof, comprising administering to the subject a therapeutically effective amount of a DNA repair enzyme inhibitor compound of Formula I, or a stereoisomer, optical isomer, a pharmaceutically acceptable salt, or a pharmaceutically acceptable solvate thereof, sufficient for inhibition of the activity of ERCC1-XPF in a cancer cell, thereby modulating drug resistance.

Described herein is a method of treating metastasis in a cancer subject in need thereof, comprising administering to the subject a therapeutically effective amount of a DNA repair enzyme inhibitor compound of Formula I, or a stereoisomer, optical isomer, a pharmaceutically acceptable salt, or a pharmaceutically acceptable solvate thereof, sufficient for inhibition of the activity of ERCC1-XPF in a cancer cell, thereby treating the metastasis.

Described herein is a method of treating cancer in a subject in need thereof, comprising administering to the subject a therapeutically effective amount of a DNA repair enzyme inhibitor compound of Formula I, or a stereoisomer, optical isomer, a pharmaceutically acceptable salt, or a pharmaceutically acceptable solvate thereof, sufficient for inhibition of the activity of ERCC1-XPF in a cancer cell, thereby treating the cancer.

Described herein is a method of inducing apoptosis in a tumor cell by inhibition of a DNA repair enzyme, comprising administering to the subject a therapeutically effective amount of a DNA repair enzyme inhibitor compound of Formula I, or a stereoisomer, optical isomer, a pharmaceutically acceptable salt, or a pharmaceutically acceptable solvate thereof, sufficient for inhibition of the activity of ERCC1-XPF in a cancer cell, thereby inducing apoptosis in the tumor cell. In certain embodiments, the tumor cell is an ovarian cancer cell. In certain embodiments, the method further comprises determining apoptosis in the tumor cell. In certain embodiments, the tumor cell is comprised in a mammal. In certain embodiments, the mammal is selected from the group consisting of a rat, a mouse, a cow, a pig and a human. In certain embodiments, the method further comprises contacting the tumor cell with a predetermined quantity of at least one compound of Formula I. In certain embodiments, the method is a method for predicting a subject's individual response to the compound. In certain embodiments, the inhibition of the DNA repair enzyme comprises an inhibition of ERCC1-XPF. In certain embodiments, the method further comprises measuring the levels of at least one component of the DNA repair protein complex.

In certain embodiments, the method further comprises comparing the result of the measurement of levels of the at least one component of at least one DNA repair enzyme complex with that of a control measurement. In certain embodiments, apoptosis is achieved by means of reactivating a binding of at least one chemotherapeutic agent to DNA and inhibiting cells from replicating. In certain embodiments, the chemotherapeutic agent comprises a platinum-containing compound. In certain embodiments, the method further comprises measuring the activity of ERCC1-XPF in the respective cell. In certain embodiments, the method further comprises comparing the result of the measurement of ERCC1-XPF activity with that of a control measurement. In certain embodiments, the inhibition of the DNA repair enzyme comprises modulating ERCC1-XPF activity in a cell that over-expresses ERCC1-XPF.

In certain embodiments, the cell is under the control of a promoter of ERCC1-XPF. Described herein is a composition for treating cancer, comprising at least one anti-proliferative agent that kills the cell via interacting with DNA, and at least one inhibitor of a DNA repair enzyme, the inhibitor comprising at least one compound of Formula I, or a stereoisomer, optical isomer, a pharmaceutically acceptable salt, or a pharmaceutically acceptable solvate thereof, in a mole ratio of the anti-proliferative agent to the inhibitor which exhibits a beneficial cytotoxic or cytostatic effect on cancer cells. In certain embodiments, the anti-proliferative agent and the inhibitor are co-encapsulated.

Described herein is a method to treat cancer in a subject which method comprises administering to a subject in need of such treatment a therapeutically effective amount of the composition described herein. In certain embodiments, the subject is a human. In certain embodiments, the subject is a non-human mammal. In certain embodiments, the cancer is ovarian cancer.

Described herein is a method of making compounds to provide a close family of analogs derived along one of Pathways A, B, C, and D, as shown in FIG. 4. In certain embodiments, the method utilizes a terminal alkyne 2e to 'click' onto biotin functionalized with an azide wherein the combined specie can then aid in purification of the binding protein(s). In certain embodiments, the derivatives synthesized in Pathways B and C, take advantage of the Tosyl functional group, including the sulfonate linkage itself. In certain embodiments, the method uses Pathway B to vary the substitution on the toluene ring. In certain embodiments, the method comprises using Pathway C, wherein compounds with differing linkers to the tosyl moiety, namely substitution of the sulfonate as a thioether (4a), sulfoxide (4b), ester (4c), and ether (4d) or amine (4e) are formed. In certain embodiments, the method comprises using Pathway D, to provide modifications of sulfonic acids. In certain embodiments, synthesized derivatives (5a-5c) having substitutions with mono- or di-carboxylates are formed.

Described herein is a biological probe comprising a compound 2b having an azido functionality.

Described herein is a method for making a DNA repair enzyme inhibitor, comprising: attaching a p-toluenesulfonic acid (Tosyl) to a phenol moiety of

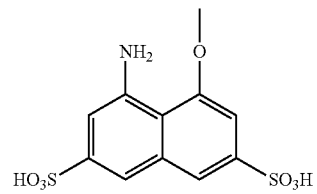

to produce compound 1.

In certain embodiments, conversion of an aromatic amine into an aromatic azide by diazotization provides a photo-probe to tag a binding protein that associates with the compound through photoaffinity labeling.

Described herein is a method for forming a DNA repair enzyme inhibitor, comprising connecting a desired moiety, via a click chemistry reaction, to a moiety having a structure:

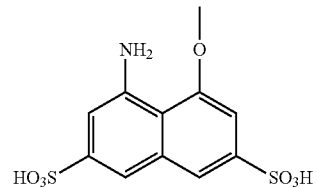

In certain embodiments, the click chemistry reaction uses an azido functionality. In certain embodiments, the click chemistry reaction uses an acetylene functionality. In certain embodiments, the click reaction is performed in the presence of a catalyst.

Various objects and advantages of this invention will become apparent to those skilled in the art from the following detailed description of the preferred embodiment, when read in light of the accompanying drawings.

DETAILED DESCRIPTION

Figure 1:
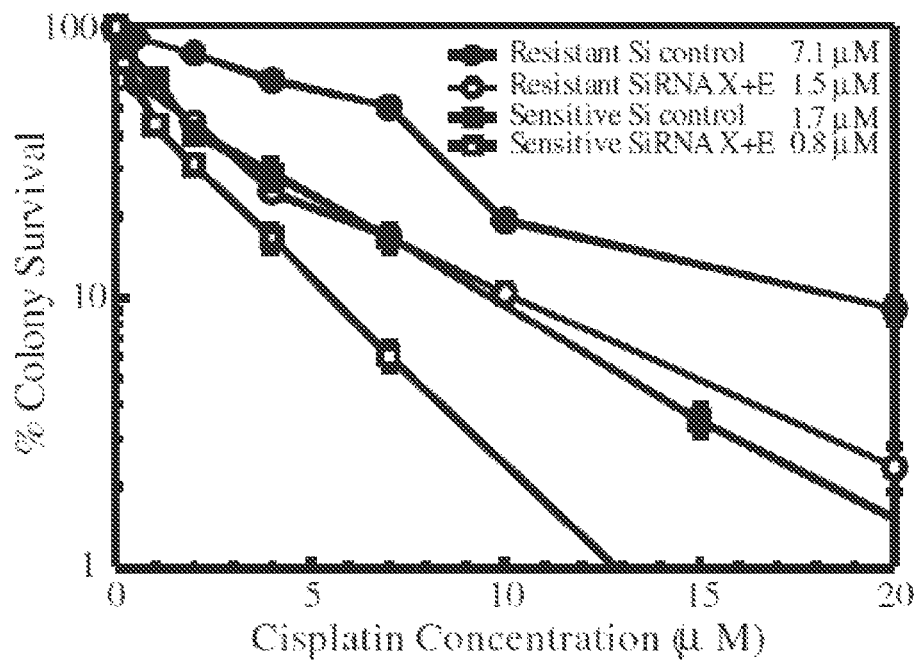
FIG. 1: Colony survival in matched ovarian cancer cell lines. 2008 (sensitive, squares) and 2008/C13*5.25 (resistant, circles) ovarian cancer cell lines were transfected with control or ERCC1-XPF siRNA and subjected to cisplatin treatment. $IC_{50}$ values are indicated.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Described herein are compositions and methods for the treatment of anti-proliferative diseases, including cancer, which comprises administering to a mammalian specie in need thereof a synergistically, therapeutically effective amount of: (1) at least one inhibitor of a DNA repair enzyme and (2) a therapeutic agent that kills cancer cells via interaction with cellular DNA.

Also described herein are compositions and methods for inhibiting the DNA repair protein complex ERCC1-XPF in order to enhance clinical responses to cisplatin and overcome drug resistance in cancer.

Definitions

The term "alkyl" refers to straight or branched chain alkane (hydrocarbon) radicals containing from 1 to 12 carbon atoms, preferably from 1 to 6 carbon atoms, and more preferably from 1 to 4 carbon atoms. Exemplary "alkyl" groups include, but are not limited to, for example, methyl, ethyl, propyl, isopropyl, n-butyl, t-butyl, pentyl, hexyl, isohexyl, heptyl, octyl, nonyl, decyl, and dodecyl.

The term "lower alkyl" refers to an "alkyl" group containing from 1 to 4 carbon atoms and preferably from 1 to 2 carbon atoms. When a subscript is used with reference to an alkyl or other group, the subscript refers to the number of carbon atoms the group may contain. For example, the term "$C_0$-$C_4$ alkyl" includes a bond and an alkyl group containing 1 to 4 carbon atoms, and the term "$C_1$-$C_4$ alkyl" refers to alkyl groups containing 1 to 4 carbon atoms. Exemplary lower alkyl groups include, but are not limited to, for example, methyl, ethyl, propyl, isopropyl, n-butyl, t-butyl, and isobutyl.

The "alkyl" group can be optionally substituted with one or more substituents, for example 1 to 4 substituents, at any available and substitutable position. Exemplary substituents include halogen (e.g., a single halo substituent or multiple halo substituents forming, in the latter case, groups such as, for example, a perfluoroalkyl group or an alkyl group bearing —$CCl_3$ or —$CF_3$), hydroxyl, —$NH_2$, —NH(alkyl), —N(alkyl)$_2$, and cyano.

The term "cycloalkyl" refers to a fully saturated hydrocarbon group containing from 1 to 4 rings and 3 to 8 carbon atoms per ring. Exemplary cycloalkyl groups include, but are not limited to, for example, cyclopropyl, cyclobutyl, cyclopentyl, cyclohexyl, and cycloheptyl. The cycloalkyl group can be optionally substituted with one or more substituents, preferably 1 to 4 substituents, at any available and substitutable point of attachment. Exemplary substituents include those groups recited for substituted alkyl.

The term "aryl" refers to cyclic aromatic hydrocarbon groups having from 1 to 2 aromatic rings, such as, for example, phenyl, biphenyl, or naphthyl. When the aryl group contains two aromatic rings (e.g., bicyclic, etc.), the aromatic rings may be joined at a single point (e.g., biphenyl) or fused (e.g., naphthyl and phenanthrenyl). The aryl group can be optionally substituted with one or more substituents, preferably 1 to 4 substituents, at any available and substitutable ring position, or where valence allows on any rings fused or attached thereto. Exemplary substituents include alkyl and those groups recited for substituted alkyl.

The terms "heterocycle" and "heterocyclic" refer to fully saturated, partially saturated, or fully unsaturated, aromatic (i.e., "heteroaryl") or nonaromatic cyclic groups that are, for example, 3 to 7 membered monocyclic or 7 to 11 membered bicyclic ring systems having at least one heteroatom in at least one carbon atom-containing ring. Each ring of the heterocycle or heterocyclic containing a heteroatom may have 1, 2, 3, or 4 heteroatoms selected from N, O, and/or S, where the N and/or S heteroatom(s) may optionally be oxidized and the N heteroatom(s) may optionally be quaternized. A heterocycle or heterocyclic may be attached to the remainder of the molecule at any heteroatom or carbon atom of the ring or ring system. The heterocycle or heterocyclic group can be substituted at any available point of attachment with at least one substituent, preferably 1 to 4 substituents, selected from alkyl and those recited for substituted alkyl.

The phrase "therapeutically effective" is intended to qualify the amount of each agent, which will achieve the goal of improvement in disorder severity and the frequency of incidence over treatment of each agent by itself, while avoiding adverse side-effects typically associated with alternative therapies. For example, effective anticancer agents prolong the survivability of the patient, inhibit the rapidly proliferating cell growth associated with the neoplasm, or effect a regression of the neoplasm.

It is to be understood that the compounds described herein may form salts which are also within the scope of this invention. The term "salt(s)" as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparations. Salts of the compounds may be formed, for example, by reacting a compound with an amount of acid or base, such as an equivalent amount, in a medium such as one in which the salt precipitates or in an aqueous medium followed by lyophilization.

The phrase "pharmaceutically acceptable salt(s)" as used herein, unless otherwise indicated, includes salts containing pharmacologically acceptable anions or cations, such as, but not limited to, the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, mesylate, saccharate, formate, benzoate, glutamate, methanesulfonate, ethanesulfonate, sulfate, benzenesulfonate, p-toluenesulfonate and pamoate salts.

Compounds form salts that can, for example, be used to isolate and/or purify the compounds. Salt(s) compounds can be formed by, for example, reacting a compound with, for example, an equivalent amount of acid or base in a medium that allows the thusly formed salt to, for example, either be precipitated out, or be isolated via lyophilization.

The term "prodrug" as employed herein denotes a compound which, upon administration to a subject, undergoes chemical conversion by metabolic or chemical processes to yield the compound or a salt thereof.

The term "patient" as used herein encompasses all mammalian species, including humans, cows, horses, dogs, and cats; and preferably, humans.

The term "purified" or "to purify" or "compositional purity" refers to the removal of components (e.g., contaminants) from a sample or the level of components (e.g., contaminants) within a sample. For example, unreacted moieties, degradation products, excess reactants, or byproducts are removed from a sample following a synthesis reaction or preparative method.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using screening methods known in the art.

The term "click chemistry" refers to chemistry tailored to generate substances quickly and reliably by joining small modular units together (see, e.g., Kolb et al. (2001) Angewandte Chemie Intl. Ed. 40:2004-2011; Evans (2007) Australian J. Chem. 60:384-395; Carlmark et al. (2009) Chem. Soc. Rev. 38:352-362; each herein incorporated by reference in its entirety).

Compositions and Uses Thereof

In another embodiment, compounds of Formula I are used:

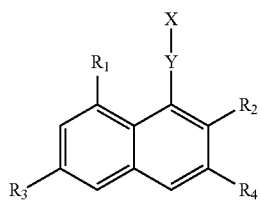

Formula I wherein: X=alkyl, alkenyl, alkynyl, aryl, or heteroaryl;

Y=$(CH_2)_n$ where n=0 to 3, CHCH, $CH_2$CHCH, CHCH$CH_2$, CC, $CH_2$CC, CC$CH_2$, O, NH, S, (SO), O(CO), (CO)O, O(CO)O, NH(CO), (CO)NH, NH(CO)NH, O(CO)NH, NH(CO)O, O($SO_2$), ($SO_2$)O, O($SO_2$)O, NH($SO_2$), ($SO_2$)NH, NH($SO_2$)NH, O(HOPO), (HOPO)O, O(HOPO)O, O(HOPO)NH, NH(HOPO)O, or NH(HOPO)NH;

$R_1$ and $R_2$ together or independently=H, alkyl, alkenyl, alkynyl, halogen, OH, $OR_5$, where $R_5$=alkyl, $NH_2$, $NHR_5$, $NR_5R_5$, or $NO_2$;

$R_3$ and $R_4$ together or independently=H providing both are not H, $CO_2H$, $CO_2X$, $SO_3H$, $SO_3X$, (HOPO)OH, or (HOPO)OX;

and where
alkyl is from 1 to 5 carbons,
alkenyl is from 2 to 6 carbons,
alkynyl is from 2 to 6 carbons,
aryl is from 6 to 12 carbons and includes aralkyl,
heteroaryl is from 5 to 12 atoms and includes heteroalkyl,
and wherein for all cases each system may be further substituted with hydroxy or amino groups.

The compounds are useful for the treatment of cancer, for example, cancers that are resistant to the effects of therapeutic agents that kill cancer cells via interacting with DNA. Thus, the treatment comprises administering to the patient the compounds of Formula I or pharmaceutically acceptable salts or prodrugs thereof in conjunction with administering a therapeutic agent that kills cancer cells via interacting with DNA.

The compounds of Formula I are especially useful for this type of treatment due to their activity as inhibitors of DNA repair protein complexes. Further, the compounds of Formula I are especially useful due to activity as inhibitors of ERCC1-XPF.

In one embodiment, a method is provided for treating cancer comprising administering to a mammal in need thereof a compound of Formula I or pharmaceutically acceptable salts thereof. The method of this embodiment can be used to treat a variety of cancers, including, but not limited to, bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, sarcomas, cytomas, melanoma, and mesothelioma.

In one embodiment, a method is provided for treating cancer comprising administering to a mammal in need thereof the compound of Formula I or pharmaceutically acceptable salts or prodrugs thereof. For example, a therapeutically effective amount of the compound of Formula I or pharmaceutically acceptable salts or prodrugs thereof may be administered in this method. A therapeutically effective amount of one or more prodrugs refers to the amount(s) of administered prodrug(s) needed to provide a therapeutically effective amount of the compound of Formula I in vivo.

In one embodiment, a compound of Formula I including pharmaceutically acceptable salts thereof, is used in the manufacture of a medicament for the treatment of cancer.

In one embodiment, a method is provided for treating cancer in a mammal wherein the cancer is resistant to chemotherapeutic drugs that function by binding to DNA and inhibiting cells from replicating and dividing, comprising administering to the patient a compound of Formula I or pharmaceutically acceptable salts thereof.

In treating cancer, a combination of chemotherapeutic agents and/or other treatments (e.g., radiation therapy) is often advantageous. The second (or third) agent may have the same or different mechanism of action than the primary therapeutic agent. It may be especially useful to employ cytotoxic drug combinations wherein the two or more drugs being administered act in different manners or in different phases of the cell cycle, and/or where the two or more drugs have nonoverlapping toxicities or side effects, and/or where the drugs being combined each has a demonstrated efficacy in treating the particular disease state manifested by the patient.

In one embodiment, a method is provided for treating cancer comprising administering to a mammal in need thereof a compound of Formula I or pharmaceutically acceptable salts or prodrugs thereof; and administering one or more additional anticancer agents.

In certain embodiments, the phrase "additional anticancer agent" refers to platinum coordination complexes, such as, but not limited to cisplatin.

Accordingly, the compounds of Formula I may be administered in combination with other anti-cancer treatments useful in the treatment of cancer or other proliferative diseases.

Also within the contemplated scope of the present invention is the use of the compounds of Formulae I and/or or pharmaceutically acceptable salts and prodrugs thereof in preparing medicaments for the treatment of cancer, and/or the packaging of the compound of Formula I herein together with instructions that the compound/s be used in combination with other anti-cancer or cytotoxic agents and treatments for the treatment of cancer. Also within the contemplated scope of present invention is the combinations of the compounds of Formula I and one or more additional agents in kit form, e.g., where they are packaged together or placed in separate packages to be sold together as a kit, or where they are packaged to be formulated together.

The compounds of Formula I can be formulated or co-administered with other therapeutic agents that are selected for their particular usefulness in addressing side effects associated with the aforementioned conditions. For example, the compounds may be formulated with agents to prevent nausea, hypersensitivity and gastric irritation, such as antiemetics, and antihistaminics.

In certain embodiments, the compounds may contain one or more additional asymmetric carbon atoms and therefore exist in two or more stereoisomeric forms. The present invention includes all of the possible individual stereoisomers, the individual tautomeric forms thereof, together with mixtures thereof. For example, separation of diastereoisomers may be achieved by any suitable technique, e.g., by fractional crystallization, chromatography or HPLC of a stereoisomeric mixture of a compound, or a suitable salt or derivative thereof. An individual enantiomer of the compound may also be prepared from a corresponding optically pure intermediate or by resolution, such as by HPLC of the corresponding racemate using a suitable chiral support or by fractional crystallization of the diastereoisomeric salts formed by reaction of the corresponding racemate with a suitable optically active acid or base, as appropriate.

Also, within the contemplated scope of the present invention are classes of pharmaceutical compositions comprising the compound of Formulae I or pharmaceutically acceptable salts and prodrugs thereof in association with one or more non-toxic, pharmaceutically-acceptable carriers and/or diluents and/or adjuvants (collectively referred to herein as "carrier" materials) and, if desired, other active ingredients. The compounds of Formulae I may be administered by any suitable route, preferably in the form of a pharmaceutical composition adapted to such a route, and in a dose effective for the treatment intended. The compounds of Formulae I and compositions comprising such compounds may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds can be processed in accordance with any suitable method of pharmacy to produce medicinal agents for administration to patients, including humans and other mammals.

For oral administration, the pharmaceutical composition may be in the form of, for example, a tablet, capsule, suspension or liquid. The pharmaceutical composition can be made in the form of a dosage unit containing a particular amount of the active ingredient. Non-limiting examples of such dosage units are tablets or capsules. In non-limiting examples, these may contain an amount of active ingredient from about 0.01 to 2000 mg, from about 1 to 500 mg, from about 5 to 150 mg, and the like. A suitable daily dose for a human or other mammal may vary widely depending on the condition of the patient and other factors, but, once again, can be determined using suitable methods.

The amounts of compounds that are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined using suitable methods. Non-limiting examples include a daily dose of: between about 0.01 to 1500 mg/kg body weight, between about 0.5 and about 50 mg/kg body weight, between about 0.1 to 20 mg/kg body weight, and the like. The daily dose can be administered in one or more doses per day.

For therapeutic purposes, the active compounds can be combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

The oily phase of the emulsions comprising compounds of Formulae I may be constituted from suitable ingredients in a suitable manner. In a non-limiting example, while the phase may comprise merely an emulsifier, it may comprise a mixture of at least one emulsifier with a fat or an oil or with both a fat and an oil. In another non-limiting example, a hydrophilic emulsifier may be included together with a lipophilic emulsifier which acts as a stabilizer. In another non-limiting example, the compositions may include both an oil and a fat.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. In non-limiting examples, the compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. The compounds may also be administered by injection as a composition with suitable carriers including saline, dextrose, or water, or with cyclodextrin, cosolvent solubilization or micellar solubilization.

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils may be employed as a solvent or suspending medium. In addition, fatty acids such as oleic acid may be used in the preparation of injectables.

The pharmaceutical compositions may be subjected to certain pharmaceutical operations such as sterilization and/or may contain suitable adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Pharmaceutical compositions comprise the compound of Formula I, or pharmaceutically acceptable salts or prodrugs thereof; and optionally one or more additional agents selected from: a kinase inhibitory agent (small molecule, polypeptide, antibody, etc.), an immunosuppressant, an anti-cancer agent, an anti-viral agent, anti-inflammatory agent, antifungal agent, antibiotic, or an anti-vascular hyperproliferation compound; and any pharmaceutically acceptable carrier, adjuvant or vehicle.

Non-limiting examples of pharmaceutically acceptable carriers, adjuvants and vehicles that may be used in the pharmaceutical compositions include: ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

Methods

Described herein are methods for inhibiting the DNA repair protein complexes, ERCC1-XPF, to enhance clinical responses to cisplatin and overcome drug resistance Inhibition of the ERCC1-XPF protein from cancer cells enhances the activity of cisplatin and overcomes drug resistance.

Targeting this protein complex in conjunction with chemotherapy is useful in treating cancers to yield better patient responses. Small molecule (drug-like) inhibitors of the ERCC1-XPF complex are now identified that block the removal of cisplatin from DNA. The inhibitors also enhance the cancer killing activity of cisplatin in cell culture models.

These ERCC1-XPF inhibitors are effective drug-like molecules. These inhibitors improve responses as well as survival rates in cancer patients.

ERCC1-XPF is a therapeutic target in ovarian cancers and other cancers that are resistant to platinum chemotherapy as well as those mutated in BRCA1/2. Targeting the ERCC1-XPF nuclease results in better clinical responses to cisplatin and platinum based chemotherapies in ovarian cancers as well as many other cancer types.

ERCC1-XPF endonuclease is required for nucleotide excision repair (NER) of helix-distorting DNA lesions. ERCC1-XPF plays a role in all cisplatin DNA repair and ERCC1-XPF protein levels inversely correlate with cisplatin sensitivity.

ERCC1-XPF is a structure specific DNA endonuclease required for NER and plays a role in some aspects of HR. The ERCC1-XPF complex is required for cisplatin intrastrand adduct repair and plays a significant role in cisplatin ICL DNA repair.

DNA excision repair protein ERCC-1 is a protein that in humans is encoded by the ERCC1 gene. The function of the ERCC1 protein is predominantly in NER of damaged DNA. ERCC1 has also been implicated as a prognostic indicator of cisplatin chemotherapy responsiveness in lung, bladder and ovarian cancer. High levels of protein are indicative of poor patient response to cisplatin treatment whereas low protein levels inversely correlates with better patient outcomes following cisplatin treatment.

It is now believed that the XPF protein can modulate cisplatin efficacy. Down-regulating ERCC1-XPF enhances cisplatin efficacy in several cancer cell lines. Down-regulating ERCC1-XPF in mouse xenograft models enhances cisplatin efficacy and survival.

Targeting ERCC1-XPF can inactivate the restored HR pathway and lead to maintained sensitivity to platinum based chemotherapy. By targeting ERCC1-XPF in BRCA1/2 defective ovarian cancers, there will be a synthetic lethality phenotype following cisplatin treatment.

In a variety of cancer cell lines, down-regulating ERCC1-XPF with siRNA enhances cisplatin efficacy 2-7 fold when comparing $IC_{50}$ values to control cell.

In order to assess whether ERCC1-XPF influences cisplatin resistance in ovarian cancer cell lines, a matched set of parental sensitive (2008s) and daughter resistant cell lines (2008/C13*5.25) were obtained. These are well characterized cell lines for assessing cisplatin resistance and effects in ovarian cancer.

As shown in FIG. 1, colony survival assays were performed in order to assess the effect of knocking down ERCC1-XPF on enhancing cisplatin efficacy. The control siRNA in this experiment shows the resistant daughter line is ~4 fold resistant to cisplatin when comparing $IC_{50}$ values to the parental sensitive cell line (filled symbols). Following greater than 90% ERCC1-XPF knockdown (data not shown), the resistant daughter cell line has a nearly 5-fold change in cisplatin sensitivity, making the cells as sensitive as the parental sensitive cell line (compare open circles with filled squares).

The sensitivity of the parental line was increased ~2 fold by targeting ERCC1-XPF. This is a significant change in drug efficacy and shows that targeting ERCC1-XPF in the clinical setting can enhance chemotherapeutic response and overcome drug resistance. This data also demonstrates that ERCC1-XPF is a valid target for enhancing cisplatin effectiveness in an established cisplatin resistant ovarian cancer cell line.

Described herein is a robust fluorescence based incision assay which was used to initially screen a diverse drug library (~2,000 compounds) in order to identify inhibitors of the ERCC1-XPF endonuclease. From the initial screen, five (5) small molecule Hits were identified that inhibited ERCC1-XPF nuclease activity with micromolar to nanomolar potency.

These Hits were further utilized in secondary and tertiary screens to assess the specificity for ERCC1-XPF and the ability to enhance cisplatin efficacy in cell culture models. The Hits identified had no inhibitory effect on two other non-related endonucleases utilizing the same assay and DNA substrate (data not shown).

Figure 2:
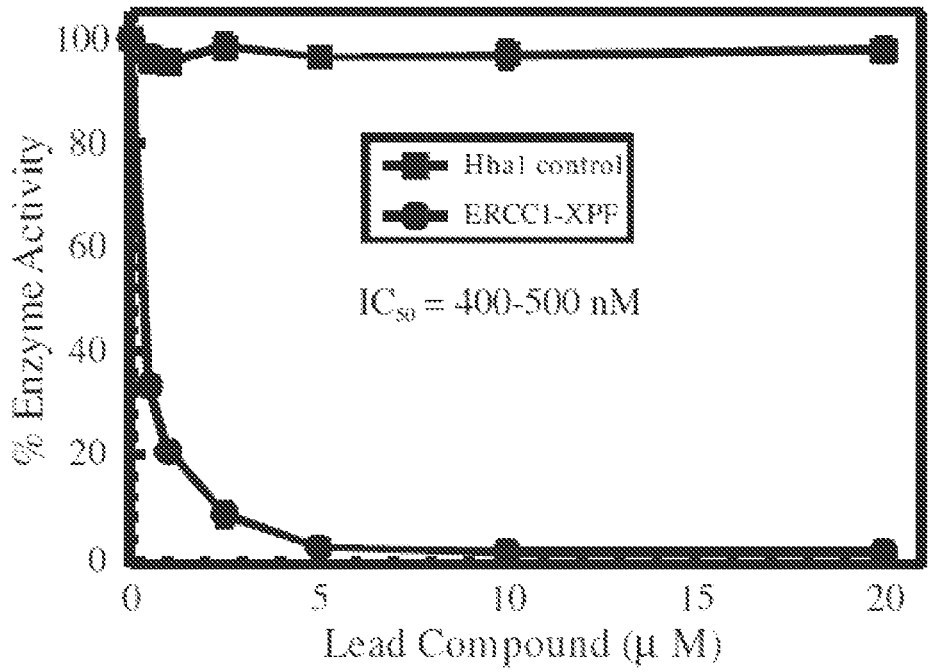
FIG. 2: Titration of lead compound in fluorescence assay. Increasing concentrations of lead compound were incubated with ERCC1-XPF or a control nuclease (Hha I) in a fluorescence based assay to assess the $IC_{50}$ values against the enzymes.

For at least one reason, the lead compound was selected based on having nanomolar potency in the fluorescence assay (FIG. 2) and having the best response in enhancing cisplatin efficacy in cell culture models. Titration of lead compound in the ERCC1-XPF fluorescence assay yields an $IC_{50}$ value of 400-500 nM (FIG. 2). As a control to ensure the lead compound was not influencing the fluorescent signal, the DNA substrate was radiolabeled and similar $IC_{50}$ values were observed.

Figures 3, 4:
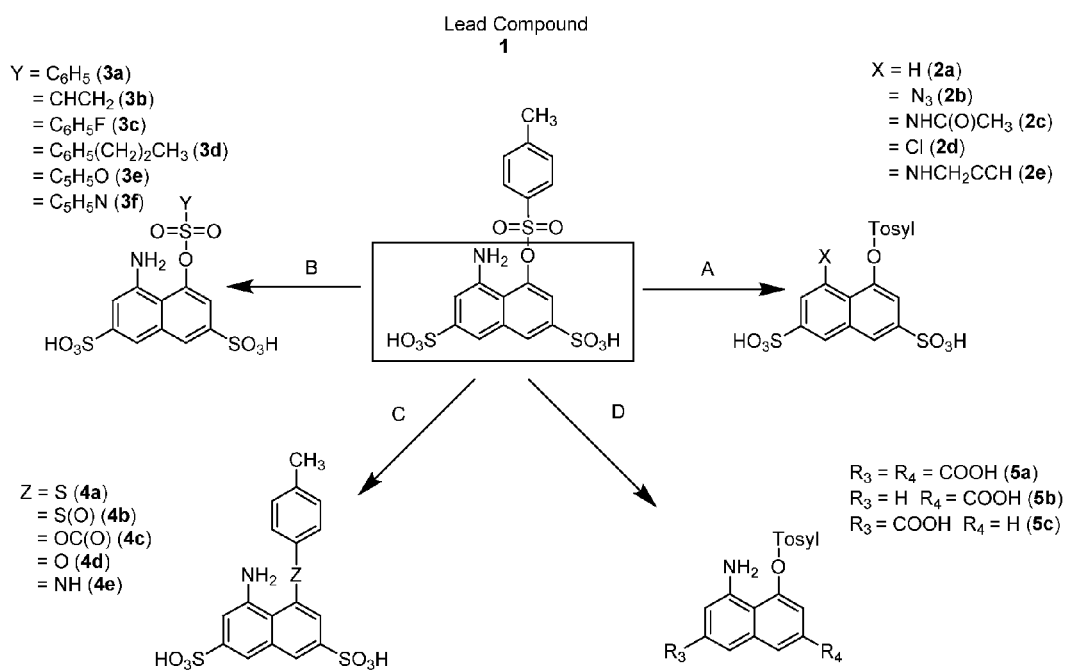
FIG. 3: Table of Combination Factor. This value is the concentration of lead compound that enhances cisplatin $IC_{50}$ values 2-fold in two different cancer cell lines.
FIG. 4: Synthetic derivatives (pathways A-D) that encompass various embodiments of the necessary functionalities associated with the activity and selectivity of lead compound (1).

The lead compound was assessed in cell culture ovarian cancer models to demonstrate that the lead compound enhances cisplatin efficacy (FIG. 3). Cells were treated with the cisplatin $IC_{50}$ concentration while the lead compound was titrated into the experiment, and colony survival assessed. The Combination Factor is the concentration of lead compound that is required to enhance cisplatin $IC_{50}$ values by 2-fold. The cisplatin resistant ovarian cancer cell line (2008/C13*5.25) has a combination factor in the low micromolar range while a lung cancer cell line (H460) has a combination factor around 7-8 µM.

Since down-regulating ERCC1-XPF inhibits cisplatin DNA repair and enhances the efficacy of cisplatin, ERCC1-XPF is a useful target to overcome cisplatin resistance. The lead compound/s described herein is a potent and selective ERCC1-XPF inhibitor.

Compounds having a desired potency were selected from in vitro assays using purified enzyme, as well as cell culture based studies that show inhibition of cisplatin DNA repair and enhanced cisplatin efficacy. The data now identify compounds that enhance cisplatin efficacy.

Methods of Making DNA Repair Enzyme Inhibitor Compounds

In FIG. 4, the boxed portion of the molecule demonstrated 50% fluorescent inhibition between 3.2-3.6 µM in the fluorescence incision assay, but had no effect in cell culture (data not shown). Interestingly, when p-toluenesulfonic acid (Tosyl) is attached to the phenol, the resulting compound 1 performed well in fluorescent and radiometric inhibition assays (50% inhibition at 400-500 nM) as well as enhancing cisplatin efficacy in cell culture ($IC_{50}$=4 µM).

As shown in FIG. 4, a number of synthetic derivatives are encompassed within the context of close chemical structure and useful biological properties. While not meant to be limiting in scope, FIG. 4 (pathways A-D) illustrate several of such derivatives as derived from the structure of lead compound 1. Each pathway takes advantage of chemically accessible positions. In addition to providing compounds having useful biological activity, compounds with azido (2b) or acetylene (2e) functionalities are useful as biological probes.

In one non-limiting example, conversion of the aromatic amine into an aromatic azide by diazotization can serve as a photoprobe to tag binding protein(s) that associate with this molecule through photoaffinity labeling. Likewise, propargyl bromide can be displaced by the aromatic amine to provide a terminal alkyne, which under click chemistry conditions, can be used to form a fluorescent tag that can confirm the location of the ligand binding to its receptor at the cellular level. Similarly, 'clicking' terminal alkyne 2e to biotin functionalized with an aromatic azide can aid in purification of the binding protein(s).

The Tosyl adduct is necessary for compound 1's ability to enhance cisplatin activity and inhibit DNA repair. Without this functionality, no activity in cell culture was observed. Derivatives synthesized in Pathways B and C, take further advantage of the Tosyl functional group, including the sulfonate linkage itself. Pathway B focuses on varying the substitution on the toluene ring. By substitution of the methyl substituent with hydrogen (3a), as well as a halogen (3c) or a propyl group (3d), steric tolerance is adjusted at this position. Alternatively, addition of a heteroatom within the aromatic ring, whether it is an oxygen (3e) or a nitrogen (3f), has little effect upon the steric environment but alters the electronic nature of this key substituent. Removal of the aromatic ring and replacement with an alkene (3b) encompasses both the steric and electronic features at this position. Pathway C exemplifies compounds with differing linkers to the tosyl moiety, namely substitution of the sulfonate as a thioether (4a), sulfoxide (4b), ester (4c), and ether (4d) or amine (4e).

In addition, Pathway D provides modifications of the sulfonic acids. Synthesized derivatives (5a-5c) represent substitutions with mono- or di-carboxylates.

In Vivo Testing

Figure 5:
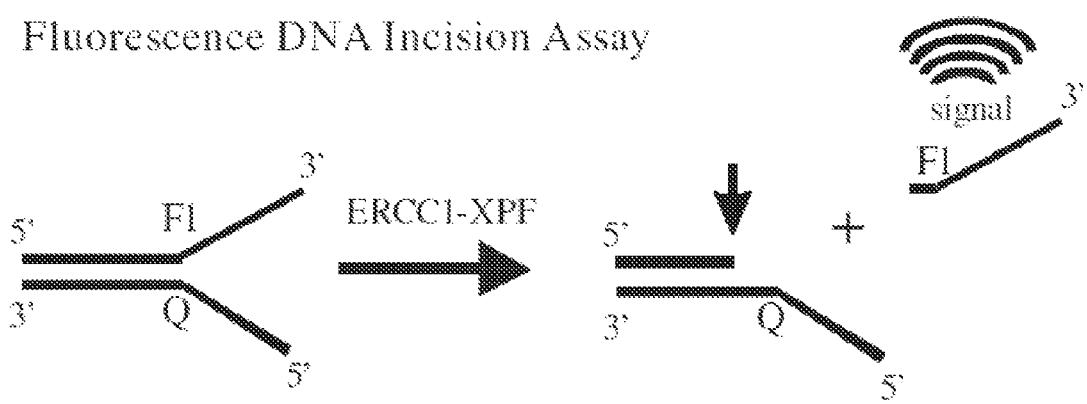
FIG. 5: Schematic illustration of a Fluorescence DNA Incision Assay.

The synthesized compounds were tested in the in vitro fluorescence incision assay and radiolabeled DNA incision assay for potency and selectivity against ERCC1-XPF. These assays are based on forked synthetic DNA substrates and purified enzyme. The fluorescent DNA substrate is designed such that a fluorophore (Fl) is incorporated into the top DNA strand while a quencher (Q) molecule is incorporated in the bottom DNA strand and in close proximity to the Fl (FIG. 5).

When the DNA substrate is annealed, the Q quenches the fluorescent signal and results in low background fluorescence. When purified ERCC1-XPF is added to the reaction, the endonuclease cleaves the DNA substrate and releases the Fl arm of the DNA from the Q DNA and an increase in fluorescent signal is observed. This assay is highly robust in a 96 well plate and has a Z' factor of 0.87. Titration of structural analogues allows for the determination of $IC_{50}$ concentrations that inhibit ERCC1-XPF and establish SAR. HhaI and XPG (both structurally and functionally distinct DNA endonucleases) were used as control enzymes to ensure the compounds are selective for ERCC1-XPF. The specific chemistry that is important for potent ERCC1-XPF inhibition is thus identified.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A compound having Formula I:

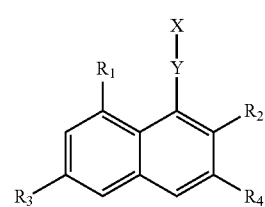

Formula I wherein: X=alkyl, alkenyl, alkynyl, aryl, or heteroaryl;
wherein:
alkyl is from 1 to 5 carbons,
alkenyl is from 2 to 6 carbons, alkynyl is from 2 to 6 carbons,
aryl is from 6 to 12 carbons and includes aralkyl,
heteroaryl is from 5 to 12 atoms and includes heteroalkyl, and wherein for all cases each system may be further substituted with hydroxy or amino groups;
Y=$(CH_2)_n$ where n=0 to 3, CHCH, $CH_2$CHCH, CHCHCH$_2$, CC, $CH_2$CC, CCCH$_2$, O, NH, S, (SO), O(CO), (CO)O, O(CO)O, NH(CO), (CO)NH, NH(CO)NH, O(CO)NH, NH(CO)O, O($SO_2$), ($SO_2$)O, O($SO_2$)O, NH($SO_2$), ($SO_2$)NH, NH($SO_2$)NH, O(HOPO), (HOPO)O, O(HOPO)O, O(HOPO)NH, NH(HOPO)O, or NH(HOPO)NH;
$R_1$ and $R_2$ together or independently=H, alkyl, alkenyl, alkynyl, halogen, OH, $OR_5$, where $R_5$=alkyl, $NH_2$, $NHR_5$, $NR_5R_5$, or $NO_2$;
$R_3$ and $R_4$ together or independently=H providing both are not H, $CO_2$H, $CO_2$X, $SO_3$H, $SO_3$X, (HOPO)OH, or (HOPO)OX; but excluding the compound wherein X is para-methylphenyl, Y is ($SO_2$)O, R1 is $NH_2$, or, Y=($SO_2$)NH with $R_1$=OH, $R_2$ is H, and $R_3$=$R_4$ are both $SO_3$H.

2. A method of treating a subject suffering from an ERCC1-XPF-associated cancer having cells that express DNA repair enzyme ERCC1-XPF, the ERCC1-XPF-associated cancers being selected from one or more of: bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, sarcomas, cytomas, melanoma, and mesothelioma,
the method comprising administering to at least one said cancer cell in need thereof:
at least one anti-cancer agent that kills cells via cross-linking DNA, and
at least one inhibitor of DNA repair enzyme ERCC1-XPF, the inhibitor comprising at least one compound of Formula I, or a stereoisomer, optical isomer, a pharmaceutically acceptable salt, or a pharmaceutically acceptable solvate thereof:

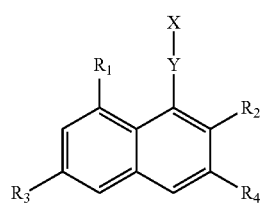

Formula I wherein: X=alkyl, alkenyl, alkynyl, aryl, or heteroaryl; wherein:
alkyl is from 1 to 5 carbons,
alkenyl is from 2 to 6 carbons,
alkynyl is from 2 to 6 carbons,
aryl is from 6 to 12 carbons and includes aralkyl,
heteroaryl is from 5 to 12 atoms and includes heteroalkyl, and wherein for all cases each system may be further substituted with hydroxy or amino groups;
Y=$(CH_2)_n$ where n=0 to 3, CHCH, $CH_2$CHCH, CHCHCH$_2$, CC, $CH_2$CC, CCCH$_2$, O, NH, S, (SO), O(CO), (CO)O, O(CO)O, NH(CO), (CO)NH, NH(CO)NH, O(CO)NH, NH(CO)O, O($SO_2$), ($SO_2$)O, O($SO_2$)O, NH($SO_2$), ($SO_2$)NH, NH($SO_2$)NH, O(HOPO), (HOPO)O, O(HOPO)O, O(HOPO)NH, NH(HOPO)O, or NH(HOPO)NH;
$R_1$ and $R_2$ together or independently=H, alkyl, alkenyl, alkynyl, halogen, OH, $OR_5$, where $R_5$=alkyl, $NH_2$, $NHR_5$, $NR_5R_5$, or $NO_2$;
$R_3$ and $R_4$ together or independently=H providing both are not H, $CO_2$H, $CO_2$X, $SO_3$H, $SO_3$X, (HOPO)OH, or (HOPO)OX.

3. The method of claim 2, wherein X is para-methylphenyl, Y is ($SO_2$)O, with $R_1$ is $NH_2$, or Y=($SO_2$)NH with $R_1$=OH, $R_2$ is H, and $R_3$=$R_4$ are both $SO_3$H.

4. The method of claim 2, wherein the at least one anti-cancer agent comprises a platinum-containing anti-neoplastic compound.

5. The method of the claim 2, wherein the anti-cancer agent is administered following administration of, prior to, or simultaneously with, compound of Formula I.

6. The method of claim 2, for the treatment of the ERCC1-XPF-associated cancer comprising ovarian cancer.

7. A pharmaceutical composition for the treatment of ERCC1-XPF-associated cancers, the RCC1-XPF-associated cancers being selected from one or more of: bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, sarcomas, cytomas, melanoma, and mesothelioma;
the composition comprising:
at least one anti-cancer agent that kills cells by cross-linking DNA, and
at least one inhibitor of DNA repair enzyme ERCC1-XPF, the inhibitor comprising at least one compound of Formula I, or a stereoisomer, optical isomer, a pharmaceutically acceptable salt, or a pharmaceutically acceptable solvate thereof, and a pharmaceutically acceptable carrier;
Formula I comprising

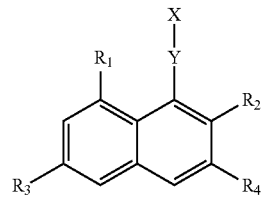

wherein: X=alkyl, alkenyl, alkynyl, aryl, or heteroaryl; wherein:
alkyl is from 1 to 5 carbons,
alkenyl is from 2 to 6 carbons,
alkynyl is from 2 to 6 carbons,
aryl is from 6 to 12 carbons and includes aralkyl,
heteroaryl is from 5 to 12 atoms and includes heteroalkyl, and wherein for all cases each system may be further substituted with hydroxy or amino groups;
Y=$(CH_2)_n$ where n=0 to 3, CHCH, $CH_2$CHCH, CHCHCH$_2$, CC, $CH_2$CC, CCCH$_2$, O, NH, S, (SO), O(CO), (CO)O, O(CO)O, NH(CO), (CO)NH, NH(CO)NH, O(CO)NH, NH(CO)O, O($SO_2$), ($SO_2$)O, O($SO_2$)O, NH($SO_2$), ($SO_2$)NH, NH($SO_2$)NH, O(HOPO), (HOPO)O, O(HOPO)O, O(HOPO)NH, NH(HOPO)O, or NH(HOPO)NH;
$R_1$ and $R_2$ together or independently=H, alkyl, alkenyl, alkynyl, halogen, OH, $OR_5$, where $R_5$=alkyl, $NH_2$, $NHR_5$, $NR_5R_5$, or $NO_2$;
$R_3$ and $R_4$ together or independently=H providing both are not H, $CO_2$H, $CO_2$X, $SO_3$H, $SO_3$X, (HOPO)OH, or (HOPO)OX.

8. The composition of claim 7, for the treatment of the ERCC1-XPF-associated cancer comprising ovarian cancer.

9. A method of treating an ERCC1-XPF-associated cancer, metastasis of an ERCC1-XPF-associated cancer and/or modulating drug resistance in an ERCC1-XPF-associated cancer subject in need thereof, the ERCC1-XPF-associated cancers being selected from one or more of: bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, sarcomas, cytomas, melanoma, and mesothelioma, the method comprising:
administering to the subject a therapeutically effective amount of at least one inhibitor of DNA repair enzyme ERCC1-XPF, the inhibitor comprising a compound of Formula I, or a stereoisomer, optical isomer, a pharmaceutically acceptable salt, or a pharmaceutically acceptable solvate thereof, sufficient for inhibition of the activity of ERCC1-XPF in the ERCC1-XPF-associated cancer cell, thereby treating the ERCC1-XPF-associated cancer, metastasis of the ERCC1-XPF-associated cancer and/or modulating drug resistance in the ERCC1-XPF-associated cancer subject;
wherein Formula I comprises

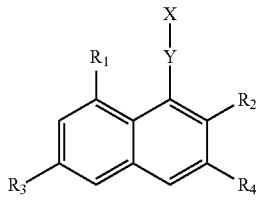

wherein: X=alkyl, alkenyl, alkynyl, aryl, or heteroaryl;
wherein:
alkyl is from 1 to 5 carbons,
alkenyl is from 2 to 6 carbons,
alkynyl is from 2 to 6 carbons,
aryl is from 6 to 12 carbons and includes aralkyl,
heteroaryl is from 5 to 12 atoms and includes heteroalkyl, and wherein for all cases each system may be further substituted with hydroxy or amino groups;

$Y=(CH_2)_n$ where n=0 to 3, CHCH, $CH_2CHCH$, $CHCHCH_2$, CC, $CH_2CC$, $CCCH_2$, O, NH, S, (SO), O(CO), (CO)O, O(CO)O, NH(CO), (CO)NH, NH(CO)NH, O(CO)NH, NH(CO)O, $O(SO_2)$, $(SO_2)O$, $O(SO_2)O$, $NH(SO_2)$, $(SO_2)NH$, $NH(SO_2)NH$, O(HOPO), (HOPO)O, O(HOPO)O, O(HOPO)NH, NH(HOPO)O, or NH(HOPO)NH;

$R_1$ and $R_2$ together or independently=H, alkyl, alkenyl, alkynyl, halogen, OH, $OR_5$, where $R_5$=alkyl, $NH_2$, $NHR_5$, $NR_5R_5$, or $NO_2$;

$R_3$ and $R_4$ together or independently=H providing both are not H, $CO_2H$, $CO_2X$, $SO_3H$, $SO_3X$, (HOPO)OH, or (HOPO)OX.

10. The composition of claim 7, wherein the anti-cancer agent and the ERCC1-XPF inhibitor are co-encapsulated.

11. The method of claim 2, wherein the subject is a human.

12. The method of claim 2, wherein the subject is a non-human mammal.

* * * * *